(12) United States Patent
Takayama (10) Patent No.: US 9,014,330 B2
(45) Date of Patent: Apr. 21, 2015

(54) RADIATION DIAGNOSTIC APPARATUS AND CONTROL METHOD

(75) Inventor: Takuzo Takayama, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 297 days.

(21) Appl. No.: 13/612,091

(22) Filed: Sep. 12, 2012

(65) Prior Publication Data

US 2013/0003918 A1 Jan. 3, 2013

Related U.S. Application Data

(63) Continuation of application No. PCT/JP2011/067737, filed on Aug. 3, 2011.

(30) Foreign Application Priority Data

Aug. 4, 2010 (JP) ................................. 2010-175461

(51) Int. Cl.
  *A61B 6/03* (2006.01)
  *A61B 6/00* (2006.01)
  *G01T 1/161* (2006.01)

(52) U.S. Cl.
  CPC .................. *A61B 6/037* (2013.01); *A61B 6/032* (2013.01); *A61B 6/4417* (2013.01); *A61B 6/54* (2013.01); *G01T 1/1612* (2013.01)

(58) Field of Classification Search
  CPC ...... A61B 6/032; A61B 6/037; A61B 6/4417; A61B 6/54; G01T 1/161; G01T 1/1611; G01T 1/1614
  USPC .............. 378/4, 19, 62, 63, 98.8; 250/363.02, 250/363.03, 363.04, 363.05, 370.09
  See application file for complete search history.

(56) References Cited

U.S. PATENT DOCUMENTS 6,449,331 B1 *  9/2002  Nutt et al. ........................ 378/19
6,490,476 B1 * 12/2002  Townsend et al. ............. 600/427
6,754,519 B1 *  6/2004  Hefetz et al. ................... 600/407
6,754,520 B2 *  6/2004  DeSilets et al. ............... 600/415

(Continued)

FOREIGN PATENT DOCUMENTS

JP  2005-106809  4/2005
JP  2006-017532  1/2006
JP  2007-107995  4/2007

OTHER PUBLICATIONS

Combined Chinese Office Action and Search Report issued Aug. 12, 2013, in Chinese Patent Application No. 201180001922.9 with English translation of category of cited documents.

(Continued)

*Primary Examiner* — Allen C. Ho
(74) *Attorney, Agent, or Firm* — Oblon, McClelland, Maier & Neustadt, L.L.P.

(57) ABSTRACT

A radiation diagnostic apparatus includes a CT gantry apparatus, a PET gantry apparatus and a controller. The CT gantry apparatus includes an X-ray tube and an X-ray detector for reconstructing an X-ray CT image. The PET gantry apparatus includes a plurality of photodetectors for reconstructing nuclear medicine images and an FE circuit that is connected to the back of the photodetectors. The controller exerts control such that, when X-rays are radiated from the X-ray tube, the output from the photodetectors to the FE circuit is stopped or reduced.

6 Claims, 8 Drawing Sheets

(56) References Cited

U.S. PATENT DOCUMENTS

| | | | |
|---|---|---|---|
| 6,810,103 B1 * | 10/2004 | Tybinkowski et al. | 378/20 |
| 6,856,666 B2 * | 2/2005 | Lonn et al. | 378/8 |
| 6,928,142 B2 * | 8/2005 | Shao et al. | 378/63 |
| 6,961,606 B2 * | 11/2005 | DeSilets et al. | 600/415 |
| 7,149,565 B2 * | 12/2006 | Kojima et al. | 600/427 |
| 7,154,096 B2 * | 12/2006 | Amano | 250/363.03 |
| 7,162,004 B2 * | 1/2007 | Inoue et al. | 378/4 |
| 7,254,438 B2 * | 8/2007 | DeSilets et al. | 600/427 |
| 7,291,840 B2 * | 11/2007 | Fritzler et al. | 250/363.05 |
| 7,292,673 B2 * | 11/2007 | Kroner et al. | 378/20 |
| 7,348,564 B2 * | 3/2008 | Wollenweber et al. | 250/363.04 |
| 7,375,337 B2 * | 5/2008 | Gagnon | 250/363.08 |
| 7,447,345 B2 * | 11/2008 | Shanmugam et al. | 382/131 |
| 7,683,338 B2 * | 3/2010 | Ueno et al. | 250/370.09 |
| 7,857,513 B2 * | 12/2010 | Li | 378/209 |
| 7,907,698 B2 * | 3/2011 | Shao et al. | 378/8 |
| 7,941,203 B2 * | 5/2011 | Zheng et al. | 600/407 |
| 8,017,914 B2 * | 9/2011 | Wollenweber et al. | 250/363.04 |
| 8,063,376 B2 * | 11/2011 | Maniawski et al. | 250/363.02 |
| 8,098,916 B2 * | 1/2012 | Thielemans et al. | 382/131 |
| 8,131,040 B2 * | 3/2012 | Koehler et al. | 382/128 |
| 8,260,013 B2 * | 9/2012 | Pekar et al. | 382/128 |
| 8,520,797 B2 * | 8/2013 | Yamada | 378/4 |
| 8,553,959 B2 * | 10/2013 | Hsieh et al. | 382/131 |
| 8,558,176 B2 * | 10/2013 | Komori et al. | 250/336.1 |
| 8,594,404 B2 * | 11/2013 | Yamaya et al. | 382/131 |
| 8,630,696 B2 * | 1/2014 | Kim et al. | 600/427 |
| 2005/0067578 A1 | 3/2005 | Ueno et al. | |
| 2011/0299655 A1 * | 12/2011 | Takayama | 378/63 |

OTHER PUBLICATIONS

International Search Report dated Nov. 1, 2011 issued for International Application No. PCT/JP2011-067737, filed Aug. 3, 2011. (w/Partial English translation).

International Written Opinion issued Nov. 1, 2011 for PCT/JP2011/067737.

* cited by examiner

RADIATION DIAGNOSTIC APPARATUS AND CONTROL METHOD

CROSS-REFERENCE TO RELATED APPLICATIONS

This application is a continuation of PCT international application Ser. No. PCT/JP2011/067737 filed on Aug. 3, 2011 which designates the United States, and which claims the benefit of priority from Japanese Patent Application No. 2010-175461, filed on Aug. 4, 2010; the entire contents of which are incorporated herein by reference.

FIELD

Embodiments described herein relate generally to a radiation diagnostic apparatus and a control method.

BACKGROUND

Conventionally, nuclear medicine imaging apparatuses, such as single photon emission computed tomography (SPECT) apparatuses and positron emission computed tomography (PET) apparatuses, are known as medical image diagnostic apparatuses that can perform functional diagnosis of the living tissue of a subject. Specifically, a nuclear medicine imaging apparatus detects, using a detector, gamma rays, which are emitted from an isotope or a labeled compound a selectively absorbed by living tissue, and then reconstructs nuclear medicine images which depict the radiation dose distribution of the detected gamma rays.

In recent years, apparatuses such as PET-CT apparatuses and SPECT-CT apparatuses have been put to practical use that are combinations of nuclear medicine imaging apparatuses and X-ray computed tomography (CT) apparatuses, which image morphological information on a living tissue of a subject. While rotating an X-ray tube and an X-ray detector about the body axis of a subject, an X-ray CT apparatus radiates X-rays from the X-ray tube to the subject and detects the X-rays that pass through the subject, thereby reconstructing images (X-ray CT images) that visualize the tissue morphology of the X-ray irradiated part of the subject.

X-ray CT apparatuses, however, generate more X-rays than gamma rays detected by PET apparatuses or SPECT apparatuses. In other words, with PET-CT apparatuses or SPECT-CT apparatuses, when acquiring X-ray CT images, scattered radiation of the X-rays generated by an X-ray CT apparatus are incident on the gamma ray detector. The incident scattered radiation may exceed the dynamic range of measurement for acquiring nuclear medicine images. When the measurement dynamic range is exceeded, a load is applied to the circuit that is connected to the gamma ray detector.

DETAILED DESCRIPTION

According to one embodiment, a radiation diagnostic apparatus includes a first gantry, a second gantry, and a controller. The first gantry includes an X-ray tube and an X-ray detector for reconstructing an X-ray CT image. The second gantry includes a plurality of photodetectors for reconstructing nuclear medicine images and a circuit connected to the back of the photodetectors. The controller is configured to exert control such that, when X-rays are radiated from the X-ray tube, output of the photodetectors to the circuit is stopped or reduced. Embodiments of a radiation diagnostic apparatus will be described in detail below with reference to the accompanying drawings. In the following description, a PET-CT apparatus obtained by integrating a positron emission computed tomography (PET) apparatus and an X-ray computer tomography (CT) apparatus, as a radiation diagnostic apparatus, will be described as embodiments.

First Embodiment

Figure 1:
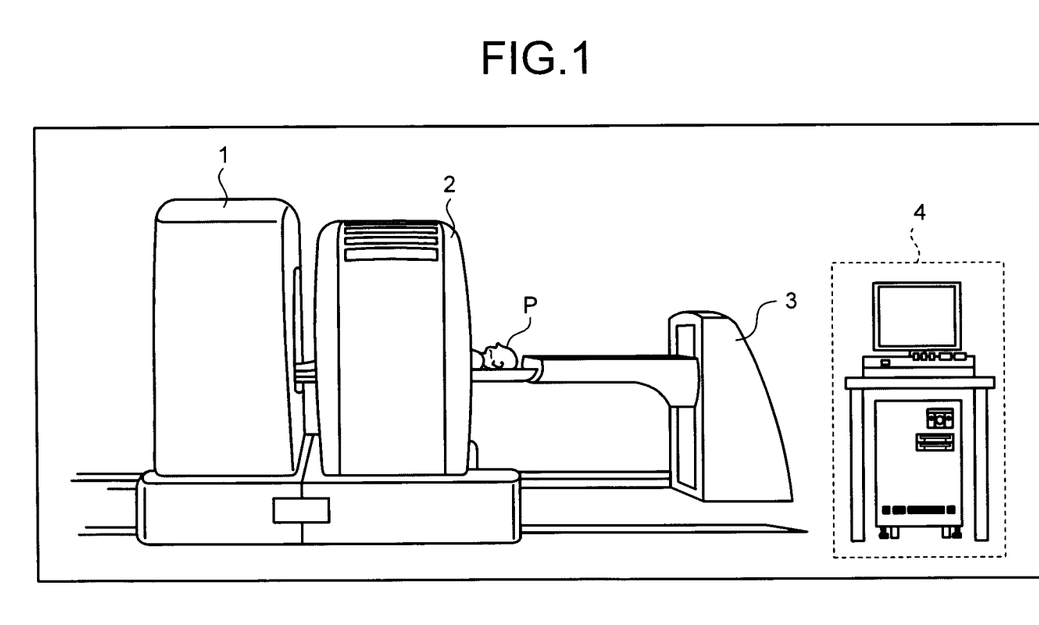
FIG. 1 is a diagram illustrating an entire configuration of a PET-CT apparatus according to a first embodiment.

First, the entire configuration of the PET-CT apparatus according to the first embodiment will be described using FIG. 1. FIG. 1 is a diagram illustrating the entire configuration of the PET-CT apparatus according to the first embodiment.

As shown in FIG. 1, the PET-CT apparatus according to the first embodiment includes a PET gantry apparatus 1, a CT gantry apparatus 2, a couch 3, and a console device 4.

Figure 2:
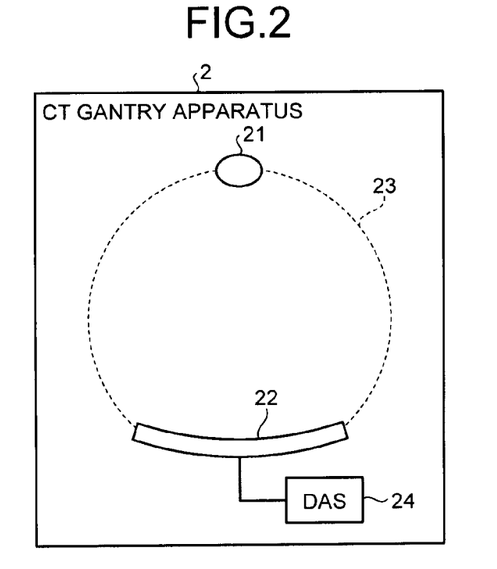
FIG. 2 is a diagram illustrating a configuration of a CT gantry apparatus.

The CT gantry apparatus 2 is an apparatus that detects X-rays that pass through a subject P, thereby generating X-ray projection data for reconstructing X-ray CT images and X-ray projection data for generating scanograms that are used to prepare an image acquisition plan. FIG. 2 is a diagram illustrating a configuration of the CT gantry apparatus.

As shown in FIG. 2, the CT gantry apparatus 2 includes an X-ray tube 21, an X-ray detector 22, a rotation frame 23, a DAS 24, and the like. The X-ray tube 21 is a device that generates X-ray beams and radiates the generated X-ray beams to the subject P. The X-ray detector 22 is a device that detects the X-rays that pass through the subject P at a position where the X-ray detector 22 is opposed to the X-ray tube 21. Specifically, the X-ray detector 22 is a two-dimensional array detector that detects data on the two-dimensional intensity distribution of the X-rays that pass through the subject P (two-dimensional X-ray intensity distribution data). More specifically, the X-ray detector 22 includes a plurality of arrays of detecting elements including X-ray detecting elements corresponding to a plurality of channels, which are arrays lined along the body axis of the subject P.

The rotation frame 23 supports the X-ray tube 21 and the X-ray detector 22 in positions where they are opposed to each other. The DAS 24 is a data acquisition system and collects the two-dimensional X-ray intensity distribution data that is detected by the X-ray detector 22. The DAS 24 performs an amplification process or an A/D conversion process on the collected two-dimensional X-ray intensity distribution data, thereby generating X-ray projection data. The DAS 24 then transmits the X-ray projection data to the console device 4 in FIG. 1.

Figure 3:
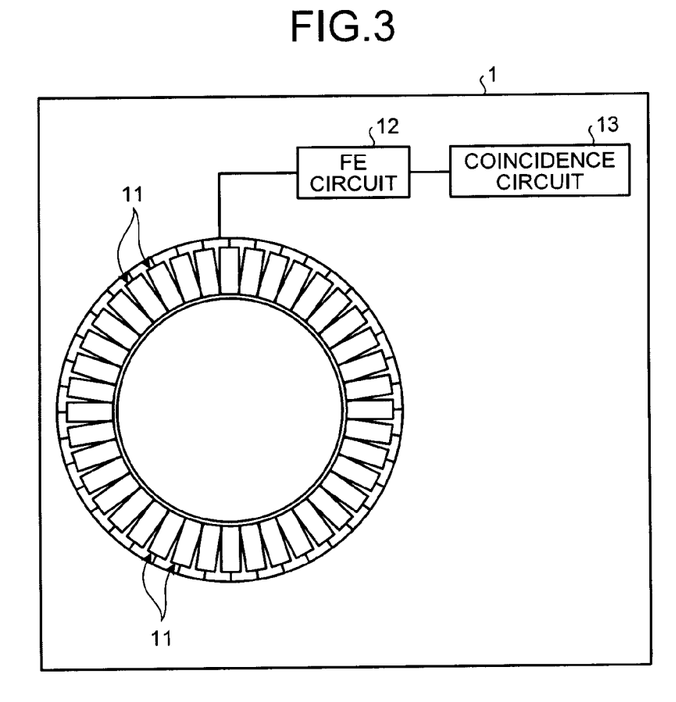
FIG. 3 is a diagram illustrating a configuration of a PET gantry apparatus.

Referring back to FIG. 1, the PET gantry apparatus 1 is an apparatus that detects a pair of gamma rays that have been emitted from a tissue that has absorbed a positron-emitting radionuclide that was applied to the subject P, thereby generating gamma-ray projection data for reconstructing PET images. FIG. 3 is a diagram illustrating a configuration of the PET gantry apparatus.

Figure 4:
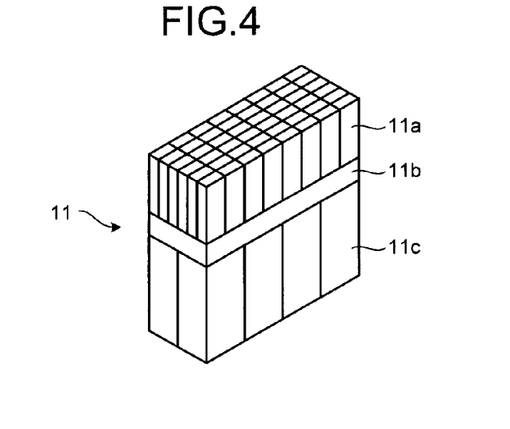
FIG. 4 is a diagram illustrating a PET detector module.

As shown in FIG. 3, the PET gantry apparatus 1 includes a plurality of PET detector modules 11, a front end (FE) circuit 12, a coincidence circuit 13, and the like. The PET detector module 11 is a photon counting type detector for detecting gamma rays that are emitted from the subject P. The PET detector is configured by arranging multiple PET detector modules 11 to surround the circumference of the subject P in a ring form. The PET detector modules 11 are not limited to the case where they are arranged in a ring form. For example, in the PET detector, multiple PET detector modules 11 may be arranged in a partial ring form. Alternatively, for example, in the PET detector, two sets of flatly aligned PET detector modules 11 may be arranged across the subject P. FIG. 4 is a diagram illustrating a PET detector module.

For example, the PET detector module 11 is an anger-type detector that includes a scintillator 11a, a photomultiplier tube (PMT) 11c that functions as an optical detector, and a light guide 11b.

The scintillators 11a adopt sodium iodide (NAI), bismuth germinate (BGO), lutetium yttrium oxyorthosilicate (LYSO), lutetium oxyorthosilicate (LSO), lutetium gadolinium oxyorthosilicate (LGSO), or the like to convert the incident gamma rays emitted from the subject P to visible light, and are arranged in two-dimensionally, as shown in FIG. 4. The photomultiplier tube 11c is a device that amplifies visible light that is output from the scintillator 11a and converts the visible light to an electric signal. As shown in FIG. 4, multiple photomultiplier tubes 11c are arranged densely via the light guide 11b. The light guide 11b is used to transmit the visible light that is output from the scintillator 11a to the photomultiplier tube 11c. The light guide 11b is made of, for example, a plastic material with excellent light transmissivity.

The photomultiplier tube 11c includes a photocathode that receives scintillation light and generates photoelectrons, multi-stage dynodes that supply an electric field to accelerate the generated photoelectrons, and a photoanode that is a port from which the electrons flow out. The electrons that are emitted from the photocathode, due to the photoelectric effect, are accelerated toward a dynode and strike the surface of the dynode so that a plurality of electrons is produced. This phenomenon is repeated over the multi-stage dynodes, thereby multiplying the number of electrons, in a way analogous to an avalanche, so that the number of electrons at the anode reaches approximately 1 million. In this example, the gain of the photomultiplier tube 11c has a millionfold increase. Usually, there is a high voltage equal to or more than 600 volts applied between the dynode and the anode because of the amplification using the avalanche phenomenon.

As described above, the scintillator 11a converts gamma rays to visible light and the photomultiplier tube 11c converts the converted visible light to an electric signal, and thereby the PET detector module 11 counts the number of gamma rays emitted from the subject P.

Figure 5A:
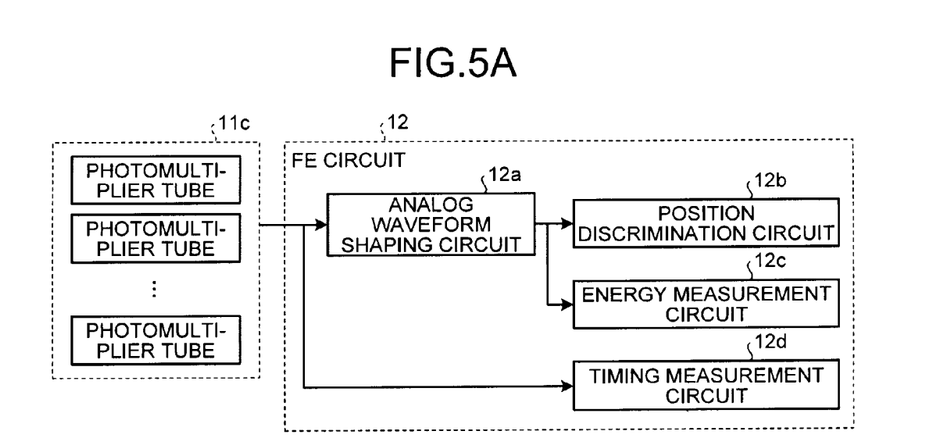
FIG. 5A is a diagram (1) illustrating a configuration of an FE circuit.
Figure 5B:
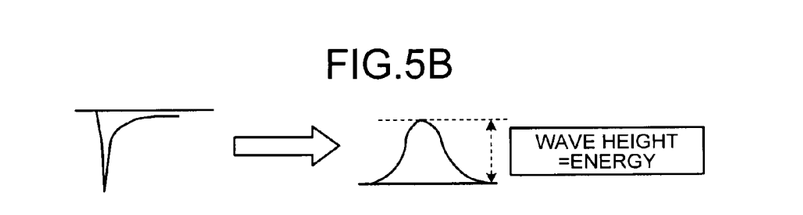
FIG. 5B is a diagram (2) illustrating the configuration of the FE circuit.

The FE circuit 12 is connected to the back of each of the photomultiplier tubes 11c of each of the PET detector modules 11 and is connected to the front of the coincidence circuit 13. According to the analog waveform data of the electric signals that are output from the photomultiplier tubes 11c, the FE circuit 12 generates various types of digital data used for the process that is performed by the coincidence circuit 13. FIGS. 5A and 5B are diagrams illustrating a configuration of the FE circuit.

As shown in FIG. 5A, the FE circuit 12 includes an analog waveform shaping circuit 12a, a position discrimination circuit 12b, an energy measurement circuit 12c, and a timing measurement circuit 12d. The analog waveform shaping circuit 12a performs a waveform shaping process on the analog waveform data of the electric signals, which are output from the photomultiplier tubes 11c. Specifically, the analog waveform shaping circuit 12a performs a calculation process (integral processing and differential processing) on the analog waveform data in the left view in FIG. 5B. Accordingly, as shown in the right view in FIG. 5B, the analog waveform shaping circuit 12a generates data whose wave height represents the energy. The analog waveform shaping circuit 12a outputs the data generated to the position discrimination circuit 12b and the energy measurement circuit 12c.

The position discrimination circuit 12b determines positions where gamma rays are incident.
Specifically, the position discrimination circuit 12b determines the positions where gamma rays are incident (the positions of the scintillators 11a) by calculating the position of the center of gravity according to the positions of the photomultiplier tubes 11c, which convert visible light output from a scintillator 11a to electric signals at the same timing and the energy that is measured using the data generated by the analog waveform shaping circuit 12a. The position discrimination circuit 12b outputs digital data of the determined positions where the gamma rays are incident to the coincidence circuit 13.

The energy measurement circuit 12c measures the energy from the data that is generated by the analog waveform shaping circuit 12a. The energy measurement circuit 12c outputs digital data on the measured energy to the coincidence circuit 13.

The timing measurement circuit 12d measures the time (timing) when the gamma rays are detected according to the analog waveform data shown in the left view of FIG. 5B. For example, the timing measurement circuit 12d measures the time point when a predetermined voltage value is exceeded in the analog waveform data shown in the left view of FIG. 5B. The timing measurement circuit 12d then outputs the digital data of the time of detection to the coincidence circuit 13.

Referring back to FIG. 3, according to various types of digital data output from the FE circuit 12, the coincidence circuit 13 generates coincidence information for determining the directions of incidence of a pair of gamma rays that are emitted from an annihilation of a positron from a radionuclide and a local electron. Specifically, the coincidence circuit 13 searches, from various types of digital data output from the FE circuit 12, a combination for which the timing of the incidence of gamma rays (time of detection) is within a time window width of a certain time period and for which the energies are both within a certain energy window width (performs coincidence finding). For example, the time window width of 2 n sec and the energy window width of 350 keV to 550 keV are set as search conditions. The coincidence circuit 13 generates coincidence counting information (coincidence list) by using the result of the output of the searched combination as information obtained by coincidently counting two annihilation photons. The coincidence circuit 13 transmits, to the console device 4 shown in FIG. 1, the coincidence counting information as gamma-ray projection data for reconstructing PET images. The line connecting the two detection positions where two annihilation photons are coincidently counted is referred to as a line of response (LOR). Alternatively, the coincidence counting information may be generated in the console device 4.

Referring back to FIG. 1, the couch 3 is a bed on which the subject P lays down. The couch 3 is sequentially moved to each of the imaging bores of the CT gantry apparatus 2 and the PET gantry apparatus 1 according to instructions received from the operator of the PET-CT via the console device 4.

In other words, the PET-CT apparatus initially acquires X-ray CT images by moving the couch 3 and then acquires PET images. For example, when acquiring X-ray CT images, the PET-CT apparatus moves the couch 3 while rotating the rotation frame 23 of the CT gantry apparatus 2, thereby performing helical scanning to helically scan an imaging region in the subject P by using X-rays. Furthermore, the PET-CT apparatus acquires PET images by moving the couch 3 such that the imaging region in the subject P is inserted into the imaging bore of the PET gantry apparatus 1.

In an examination using the PET-CT apparatus, scanograms obtained by scanning the whole body of the subject P along the body-axis direction are acquired by moving the couch 3 while X-rays are radiated from the X-ray tube 21 with the rotation frame 23 being fixed. The operator, who refers to the scanograms of the subject P, prepares a plan to acquire X-ray CT images and PET images.

Figure 6:
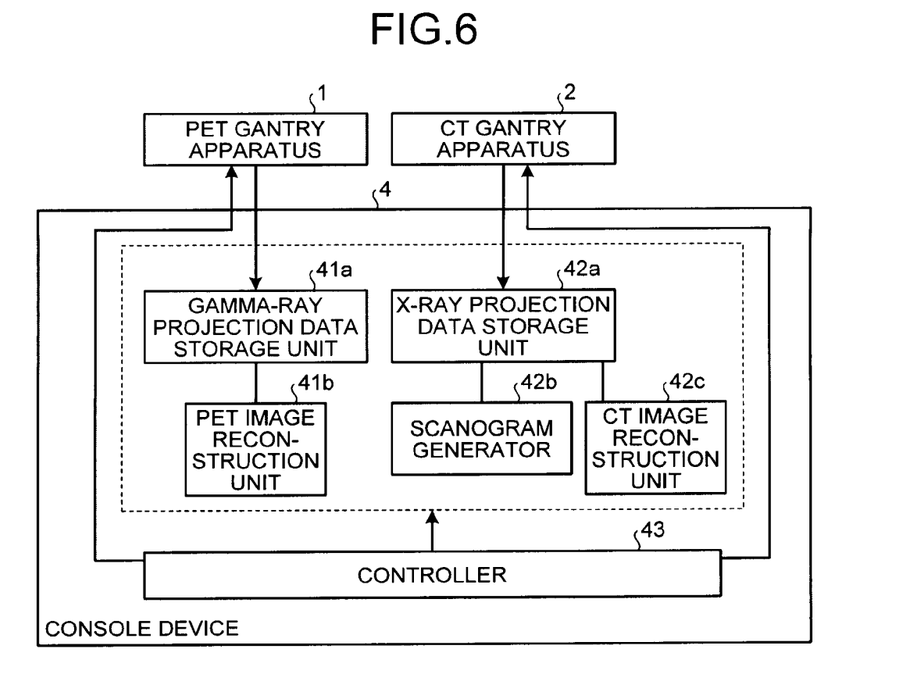
FIG. 6 is a diagram illustrating a configuration of a console device.

The console device 4 is a device for receiving instructions from the operator and controlling the image acquisition process performed by the PET-CT apparatus. FIG. 6 is a diagram illustrating a configuration of the console device.

As shown in FIG. 6, the console device 4 includes a gamma-ray projection data storage unit 41a, a PET image reconstruction unit 41b, an X-ray projection data storage unit 42a, a scanogram generator 42b, and a CT image reconstruction unit 42c. As shown in FIG. 6, the console device 4 further includes a controller 43.

The X-ray projection data storage unit 42a stores the X-ray projection data transmitted from the DAS 24. Specifically, the X-ray projection data storage unit 42a stores X-ray projection data for generating scanograms and X-ray projection data for reconstructing X-ray CT images.

The scanogram generator 42b generates scanograms from the X-ray projection data for generating scanograms, which is the data stored in the X-ray projection data storage unit 42a. The CT image reconstruction unit 42c reconstructs the X-ray CT images by performing back-projection, for example, according to a filtered back projection (FBP) method, on the reconstruction of the X-ray projection data stored in the X-ray projection data storage unit 42a.

In other words, the scanogram generator 42b generates scanograms for preparing an image acquisition plan for a whole-body examination using the PET-CT apparatus. In addition, in the whole-body examination using the PET-CT apparatus, the CT image reconstruction unit 42c reconstructs a plurality of X-ray CT images obtained by acquiring images of a plurality of cross-sections perpendicular to the body-axis direction of the subject P by using the generated X-ray projection data according to the image acquisition conditions (such as the slice width) determined by the image acquisition plan.

The gamma-ray projection data storage unit 41a stores the gamma-ray projection data that is transmitted from the coincidence circuit 13. The PET image reconstruction unit 41b reconstructs the PET images from the gamma-ray projection data stored in the gamma-ray projection data storage unit 41a by using successive approximations, such as a maximum likelihood expectation maximization (MLEM) method or an ordered subset MLEM (OSEM) method.

The controller 43 controls the whole process performed by the PET-CT apparatus. Specifically, the controller 43 controls the image acquisition by the PET-CT apparatus by controlling the PET gantry apparatus 1 and the CT gantry apparatus 2. In addition, the controller 43 controls the process performed by the PET image reconstruction unit 41b using the data stored in the gamma-ray projection data storage unit 41a. In addition, the controller 43 controls the process performed by the scanogram generator 42b and the CT image reconstruction unit 42c using the data stored in the X-ray projection data storage unit 42a. In addition, the controller 43 receives instructions form the operator via an input/output device (not shown). The controller 43 further exerts control such that a graphical user interface (GUI) for allowing the operation to enter instructions, a scanogram, an X-ray CT image, or a PET image is displayed on the input/output device (not shown).

The entire configuration of the PET-CT apparatus according to the first embodiment is described above. The PET-CT apparatus configured as described above according to the first embodiment acquires X-ray CT images and PET images.

In the PET image acquisition, when gamma rays that are emitted from an annihilation of a positron that is absorbed by a tissue of the subject P are measured, the counting rate (cps: count per sec) at which gamma rays are measured by the PET detector module 11 is usually within a range of 300 to 500 Mcps. In addition, as described above, a high voltage is applied to the photomultiplier tubes 11c. For this reason, when the power supply to the photomultiplier tube 11c in the off state is turned on, it takes, for example, about two hours to stabilize the output of the photomultiplier tube 11c. For this reason, normally, a high voltage is kept supplied to the photomultiplier tubes 11c.

When scanograms or X-ray CT images are acquired, the scattered radiation of the X-rays generated by the X-ray tube 21 is incident on the PET detector modules 11. The PET detector modules 11 to which a high voltage is being supplied also measure the scattered radiation of the X-rays. The data obtained by measuring the scattered radiation is output from the photomultiplier tubes 11c to the FE circuit 12. However, the counting rate at which scattered radiation is measured may be 100 times or 1000 times greater than the measurement rate in the case of acquiring PET images.

Thus, the analog waveform shaping circuit 12a also performs a process on the analog waveform data of electric signals originating from the scattered radiation and, due to the high counting rate, analog waveform data is sequentially input during the calculation process. In other words, in the FE circuit 12, data to be processed is piled up. This applies a load to the analog waveform shaping circuit 12a, which may cause a failure in the FE circuit 12.

Therefore, in the PET-CT apparatus according to the first embodiment, control by the controller 43, which will be described in detail below, is performed.

Figure 7A:
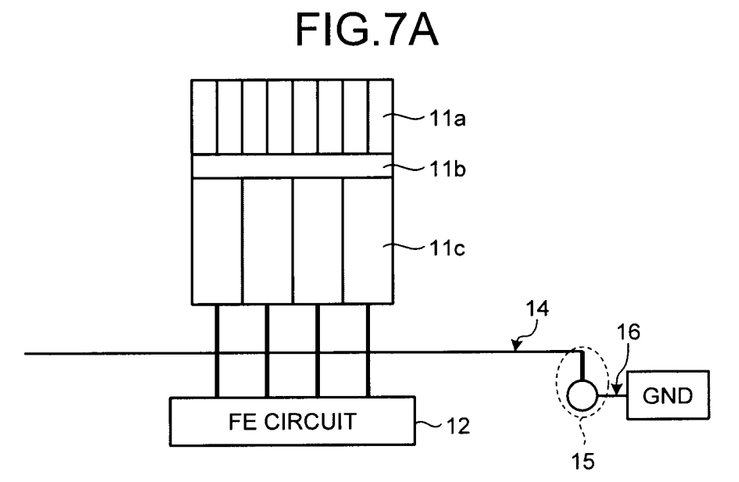
FIG. 7A is a diagram (1) illustrating a controller according to the first embodiment.
Figure 7B:
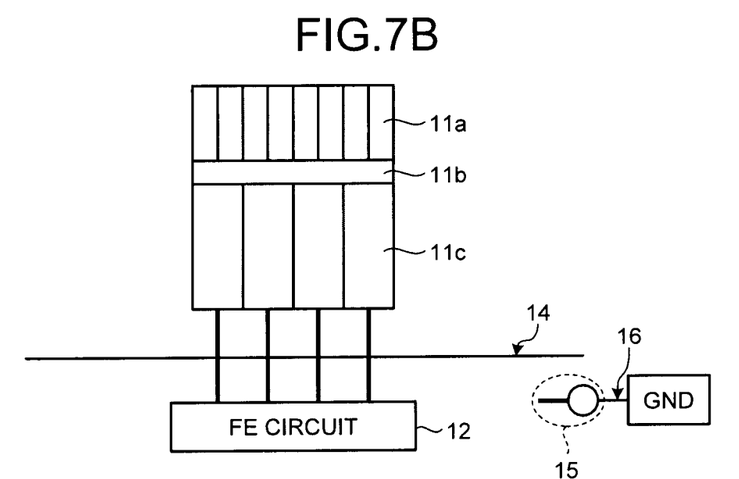
FIG. 7B is a diagram (2) illustrating the controller according to the first embodiment.

In other words, the controller 43 exerts control such that, when X-rays are radiated from the X-ray tube 21, the output from the photomultiplier tubes 11c to the FE circuit 12 is stopped. Specifically, the controller 43 exerts control such that, when X-rays are radiated from the X-ray tube 21, the output from the photomultiplier tubes 11c is grounded. FIGS. 7A and 7B are diagrams illustrating the controller according to the first embodiment.

For example, in the first embodiment, as shown in FIG. 7A, the PET gantry apparatus 1 is provided with a bypass wiring 14 that bypasses an output wiring from each of the photomultiplier tubes 11c to the FR circuit 12, a switch 15, and a grounding wire 16. The switch 15 is used to connect the bypass wiring 14 and the grounding wire 16 and to disconnect the bypass wiring 14 and the grounding wire 16.

For example, during a period of time between the start of acquiring scanograms and ending of acquiring X-ray CT images, the controller 43 controls the switch 15 such that it connects the bypass wiring 14 and the grounding wire 16, as shown in FIG. 7A. Accordingly, all the output of the photomultiplier tubes 11c is grounded (GND).

When the X-ray radiation from the X-ray tube 21 ends, the controller 43 controls the switch 15 such that it disconnects the bypass wiring 14 and the grounding wire 16 for acquiring PET images, as shown in FIG. 7B. Accordingly, all the output of the photomultiplier tubes 11c is output to the FE circuit 12.

Figure 8:
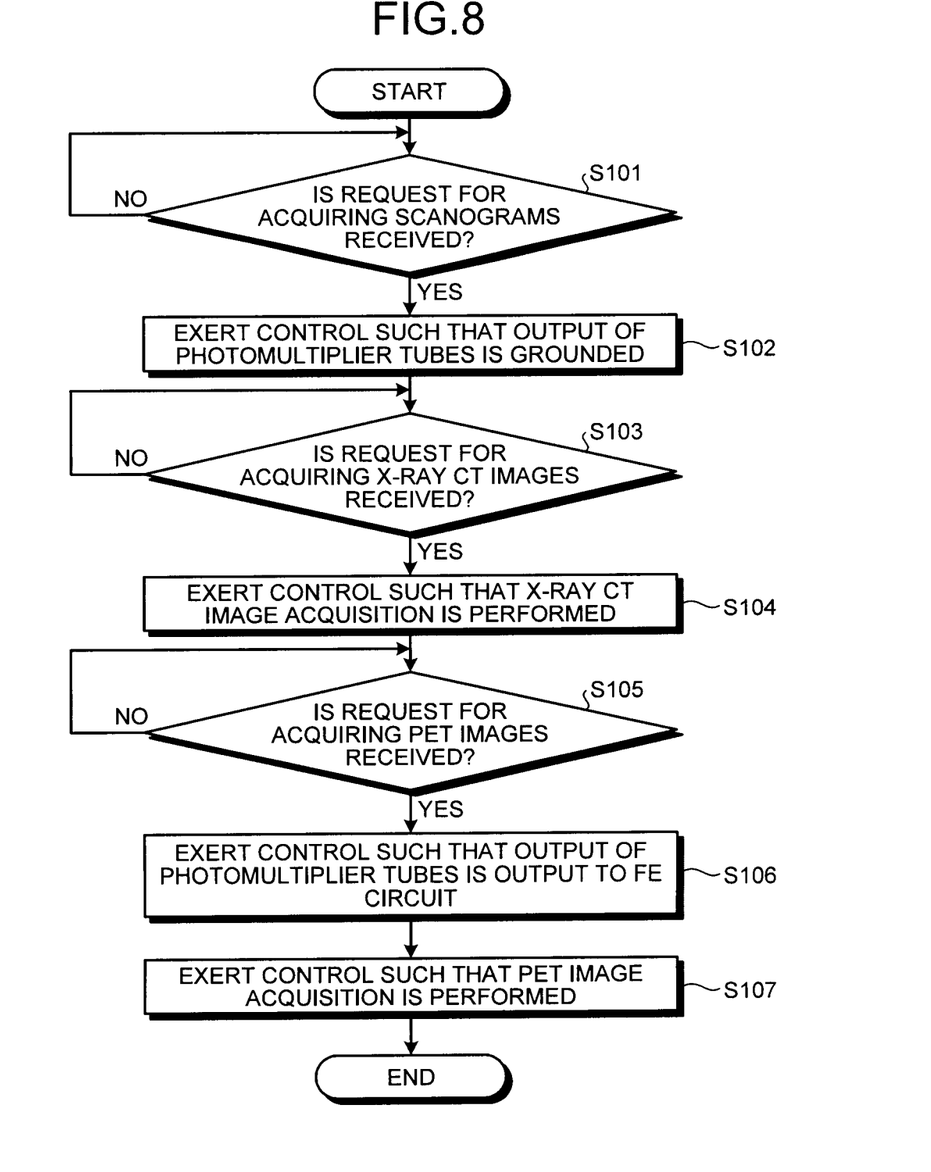
FIG. 8 is a flowchart illustrating a process performed by the PET-CT apparatus according to the first embodiment.

The process performed by the PET-CT apparatus according to the first embodiment will be described using FIG. 8. FIG. 8 is a flowchart illustrating the process performed by the PET-CT apparatus according to the first embodiment.

As shown in FIG. 8, the PET-CT apparatus according to the first embodiment determines whether a request for acquiring scanograms is received (step S101). When no request for acquiring scanograms is received (NO at step S101), the PET-CT apparatus enters a standby state.

In contrast, when a request for acquiring scanograms is received (YES at step S101), the controller 43 exerts control such that the output of the photomultiplier tubes 11c is grounded (step S102). Thereafter, the controller 43 controls the CT gantry apparatus 2 so that scanogram acquisition is performed and thus the scanogram generator 42b generates scanograms.

The controller 43 then determines whether a request for acquiring X-ray CT images is received (step S103). When no request for acquiring X-ray CT images is received (NO at step S103), the PET-CT apparatus enters a standby state. In contrast, when a request for acquiring X-ray CT images is received (YES at step S103), the controller 43 exerts control the CT gantry apparatus 2 such that it performs X-ray CT image acquisition (step S104). Accordingly, the CT image reconstruction unit 42c reconstructs X-ray CT images.

The controller 43 then determines whether a request for acquiring PET images is received (step S105). When no request for acquiring PET images is received (NO at step S105), the PET-CT apparatus enters a standby state.

In contrast, when a request for acquiring PET images is received (YES at step S105), the controller 43 exerts control such that the FE circuit 12 is caused to output the output from the photomultiplier tubes 11c (step S106). The controller 43 then exerts control the PET gantry apparatus 1 such that it performs PET image acquisition (step S107) and ends the process. A scanogram acquisition request, an X-ray CT image acquisition request, or a PET image acquisition request is transferred to the controller 43 each time the operator operates the input/output device of the console device 4.

As described above, in the first embodiment, the CT gantry apparatus 2 includes the X-ray tube 21 and the X-ray detector 22 for reconstructing X-ray CT images. The PET gantry apparatus 1 includes the photomultiplier tubes 11c for reconstructing nuclear medicine images (PET images) and the FE circuit 12, which are connected to the back of the photomultiplier tubes 11c. The controller 43 exerts control such that, when X-rays are radiated from the X-ray tube 21, the output from the photomultiplier tubes 11c to the FE circuit 12 is stopped. Specifically, the controller 43 exerts control such that, when X-rays are emitted from the X-ray tube 21, the output from the photomultiplier tubes 11c is grounded.

Accordingly, according to the first embodiment, the data obtained by measuring the scattered radiation of X-rays can be prevented from being output to the FE circuit 12. As a result, according to the first embodiment, a failure due to X-ray scattering can be avoided.

In the first embodiment, the case is described in which, when X-rays are radiated from the X-ray tube 21, all the output from the photomultiplier tubes 11c to the FE circuit 12 is stopped. However, the first embodiment may be a case where, when X-rays are radiated from the X-ray tube 21, the output from the photomultiplier tubes 11c to the FE circuit 12 is reduced.

Figure 9:
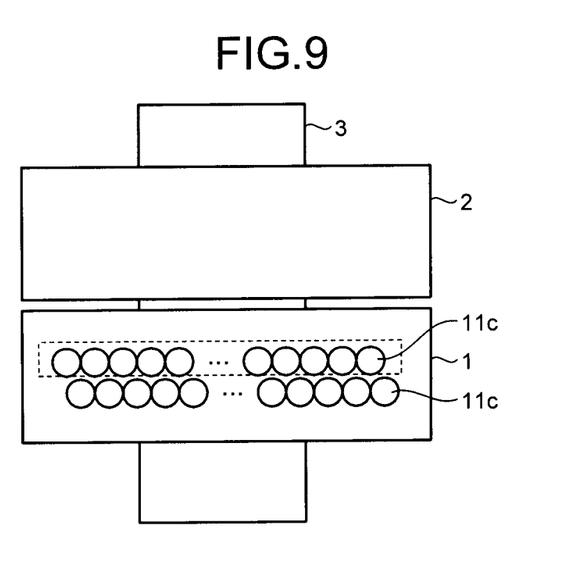
FIG. 9 is a diagram illustrating a modification of a control process performed by the controller according to the first embodiment.

In other words, the controller 43 exerts control such that, when X-rays are radiated from the X-ray tube 21, the output from a part of the photomultiplier tubes 11c is grounded. Specifically, the controller 43 exerts control such that, when X-rays are radiated from the X-ray tube 21, the output from the photomultiplier tubes 11c, which are adjacent to the CT gantry apparatus 2, out of the photomultiplier tubes 11c is grounded. FIG. 9 is a diagram illustrating a modification of the control process performed by the controller according to the first embodiment.

The diagram of FIG. 9 is an overhead schematic view of the PET-CT apparatus in FIG. 1. As shown in FIG. 9, in the PET-CT apparatus, the PET gantry apparatus 1 and the CT gantry apparatus 2 are arranged in parallel along the couch 3. In this case, the photomultiplier tubes 11c in the PET gantry apparatus 1 can be categorized into a group adjacent to the CT gantry apparatus 2 and a group apart from the CT gantry apparatus 2. For example, in the PET detector module 11 in FIG. 4, the photomultiplier tubes 11c are arranged in two lines along the longitudinal direction of the couch 3. In this case, the group adjacent to the CT gantry apparatus 2 includes the photomultiplier tubes 11c in a dotted-line rectangle in FIG. 9.

The controller 43 in the modification performs the grounding control process on the photomultiplier tubes 11c in the dotted-line rectangle in FIG. 9. For example, only the output wiring of the photomultiplier tubes 11c adjacent to the CT gantry apparatus 2 is provided with the bypass wiring 14, whereby the controller 43 performs the grounding control process.

As described above, in the modification, control is exerted such that, when X-rays are emitted, the output from the photomultiplier tubes 11c with high possibility of incidence of X-ray scattered radiation is grounded. As a result, because the counting rate of X-ray scattered radiation can be reduced, a failure due to X-ray scattering can be avoided.

The above-described modification may be a case where control is exerted such that the output from a selected part of the photomultiplier tubes 11c is grounded. For example, if there are 500 photomultiplier tubes 11c, an arbitrarily selected half of the photomultiplier tubes 11c, i.e., 250 photomultiplier tubes 11c, may be provided with the bypass wiring 14. In such a case, because the counting rate of the X-ray scattered radiation can be reduced, a failure due to X-ray scattering can be avoided.

Second Embodiment

Figure 10:
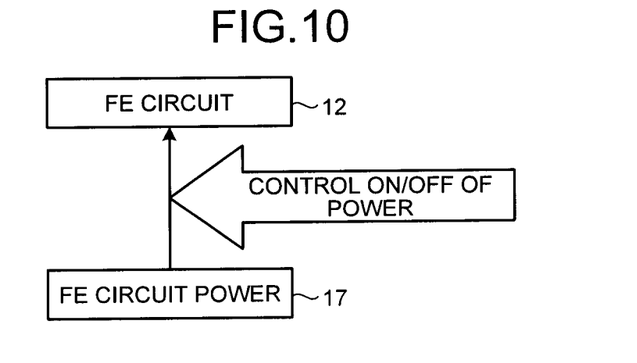
FIG. 10 is a diagram illustrating a controller according to a second embodiment.

In a second embodiment, a case will be described, using FIG. 10, in which the output from the photomultiplier tubes 11c to the FE circuit 12 is stopped by using a method different from that of the first embodiment. FIG. 10 is a diagram illustrating a controller according to the second embodiment.

The console device 4 of the PET-CT apparatus according to the second embodiment is configured like the console device 4 of the PET-CT apparatus according to the first embodiment, which is described using FIG. 6, but the control process performed by the controller 43 is different from that of the first embodiment.

The controller 43 according to the second embodiment exerts control such that, when X-rays are radiated from the X-ray tube 21, the power supply to the FE circuit 12 is stopped. In other words, as shown in FIG. 10, the controller 43 controls on/off of an FE circuit power 17. For example, the controller 43 turns off the FE circuit power 17 in a period of time from the start of acquisition of acquiring until the end of acquiring X-ray CT images. Conversely, when X-ray radiation from the X-ray tube 21 ends, the controller 43 turns on the FE circuit power 17 for acquisition of the PET images.

Figure 11:
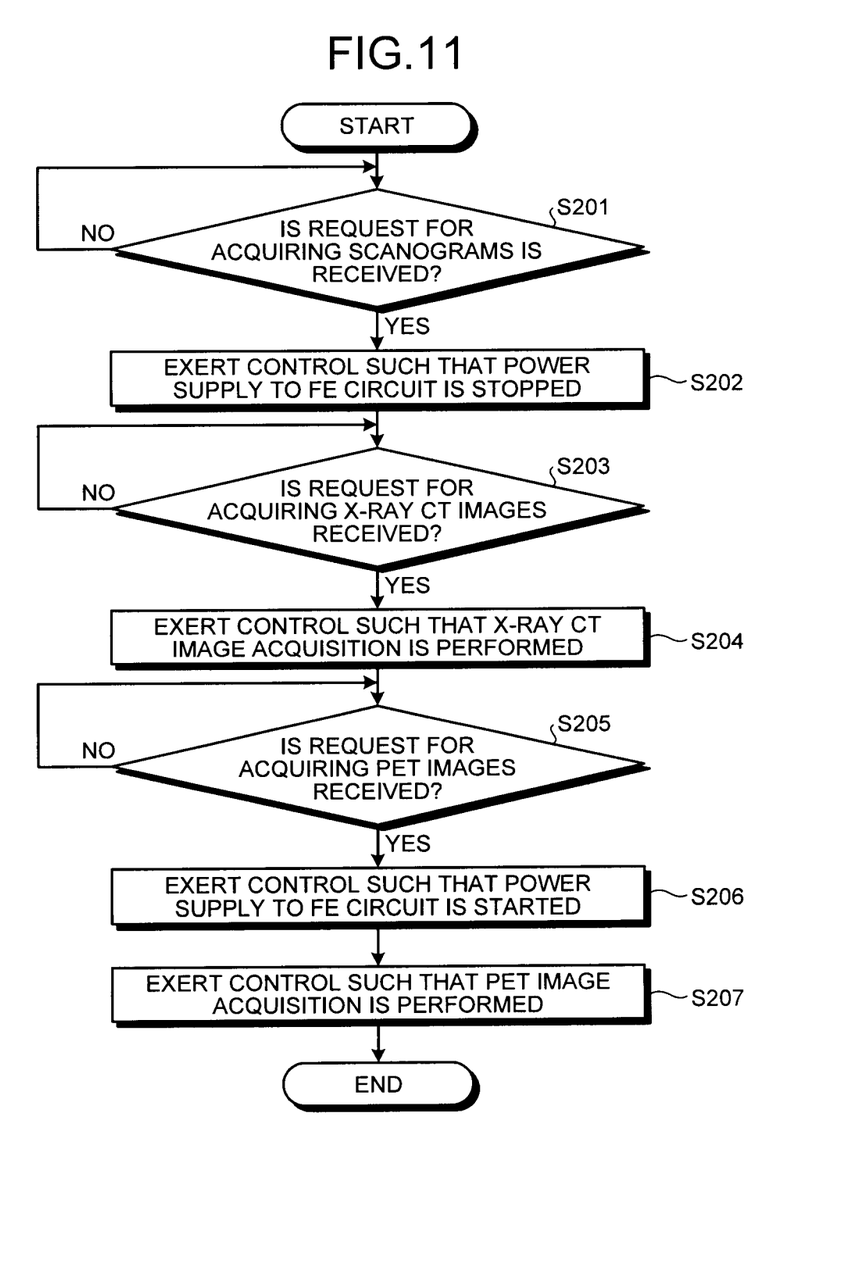
FIG. 11 is a flowchart illustrating the process performed by the PET-CT apparatus according to the second embodiment.

The process performed by the PET-CT apparatus according to the second embodiment will be described using FIG. 11. FIG. 11 is a flowchart illustrating the process performed by the PET-CT apparatus according to the second embodiment.

As shown in FIG. 11, the PET-CT apparatus according to the second embodiment determines whether a request from an operator for acquiring scanograms is received (step S201). When no request from the operator for acquiring scanograms is received (NO at step S201), the PET-CT apparatus enters a standby state.

In contrast, when a request from an operator for acquiring scanograms is received (YES at step S201), the controller 43 exerts control such that the power supply from the FE circuit power 17 to the FE circuit 12 is stopped (step S202). Thereafter, the controller 43 controls the CT gantry apparatus 2 so that scanogram acquisition is performed and thus the scanogram generator 42b generates scanograms.

The controller 43 then determines whether a request for acquiring X-ray CT images is received (step S203). When no request for acquiring X-ray CT images is received (NO at step S203), the PET-CT apparatus enters a standby state. In contrast, when a request for acquiring X-ray CT images is received (YES at step S203), the controller 43 exerts control the CT gantry apparatus 2 such that it perform X-ray CT image acquisition (step S204). Accordingly, the CT image reconstruction unit 42c reconstructs X-ray CT images.

The controller determines whether a request for acquiring PET images is received (step S205). When no request for acquiring PET images is received (NO at step S205), the PET-CT apparatus enters a standby state.

In contrast, when a request for acquiring PET images is received (YES at step S205), the controller 43 exerts control such that the power supply from the FE circuit power 17 to the FE circuit 12 is started (step S206). The controller 43 then exerts control the PET gantry apparatus 1 such that it performs PET image acquisition (step S207) and the controller 43 ends the process.

As described above, in the second embodiment, the controller 43 exerts control such that, when X-rays are emitted from the X-ray tube 21, the power supply from the FE circuit power 17 to the FE circuit 12 is stopped.

Thus, according to the second embodiment, the data obtained by measuring the scattered radiation of X-rays can be prevented from being processed by the FE circuit 12. As a result, a failure due to X-ray scattering can be avoided. Because the voltage supplied to the FE circuit 12 is low, the output of the FE circuit 12 is stabilized in a short period of time after the power supply is restarted.

In the first and second embodiments, the case is described where, during the period of time from the start of acquiring scanograms until the end of acquisition of X-ray CT images, the grounding control process or the power supply stop process is performed. In the scanogram acquisition, normally, X-rays whose dose is lower than dose of X-rays for X-ray CT image acquisition are emitted. Thus, the X-ray dosage used for scanogram acquisition can be adjusted so as not to exceed the dynamic range of the FE circuit 12. In such a case, the controller 43 performs the grounding process or the power supply stop process only during the period in which X-ray CT images are acquired. In the first and second embodiments, the case is described where the PET detector module 11 includes the photomultiplier tubes 11c as a photodetector. However, the first and second embodiments may be applied to a case where the PET detector module 11 includes a photodetector using a semiconductor device instead of the photomultiplier tubes 11c. An example of such a photodetector is a silicon photomultiplier (SiPM) using, as a semiconductor device array, avalanche photodiodes (APD).

In the first and second embodiments, the case is described where the PET-CT apparatus performs the grounding control process or the power supply stop process. However, the grounding control process and the power supply stop process that are described in the first and second embodiments can be used for a SPECT-CT apparatus that is a combination of a SPECT apparatus and an X-ray CT apparatus that use a similar detector as that of the PET apparatus.

The control methods described in the first and second embodiments can be performed by executing a prepared control program with a computer such as a personal computer or a work station. The program can be distributed through a network, such as Internet. Furthermore, the program may be recorded in a computer readable recording medium, such as a hard disk, a floppy disk (FD), a CD-ROM, an MO, or a DVD, read from the recording medium and thus executed by the computer.

As described above, according to the first and second embodiments, a failure due to X-ray scattering can be avoided.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A radiation diagnostic apparatus comprising:
a first gantry including an X-ray tube and an X-ray detector for reconstructing an X-ray computed tomography (CT) image;
a second gantry including a plurality of photodetectors for reconstructing nuclear medicine images and a circuit connected to a back of the plurality of photodetectors; and
a controller configured to exert a control such that, when X-rays are radiated from the X-ray tube, output of the plurality of photodetectors to the circuit is stopped or reduced.

2. The radiation diagnostic apparatus according to claim 1, wherein the controller exerts the control such that, when the X-rays are radiated from the X-ray tube, the output of the plurality of photodetectors is grounded.

3. The radiation diagnostic apparatus according to claim 1, wherein the controller exerts the control such that, when the X-rays are radiated from the X-ray tube, the output of a part of the plurality of photodetectors is grounded.

4. The radiation diagnostic apparatus according to claim 3, wherein the controller exerts the control such that, when the X-rays are radiated from the X-ray tube, the output of plurality of photodetectors adjacent to the first gantry out of the plurality of photodetectors is grounded.

5. The radiation diagnostic apparatus according to claim 1, wherein the controller exerts the control such that, when the X-rays are radiated from the X-ray tube, a power supply to the circuit is stopped.

6. A control method comprising:
   exerting, by a controller, a control such that, when X-rays are radiated from an X-ray tube, output of a plurality of photodetectors for reconstructing a nuclear medicine image to a circuit that is connected to a back of the plurality of photodetectors is stopped or reduced.

* * * * *